United States Patent [19]

Hanamoto et al.

[11] 4,389,491

[45] Jun. 21, 1983

[54] METHOD AND KIT FOR CHROMATOGRAPHIC SEPARATION OF HEMOGLOBIN $A_{1c}$

[75] Inventors: Mark S. Hanamoto, Mill Valley; Steve K. Tanaka, Vallejo, both of Calif.

[73] Assignee: Bio-Rad Laboratories, Inc., Richmond, Calif.

[21] Appl. No.: 371,844

[22] Filed: Apr. 26, 1982

[51] Int. Cl.³ ............... G01N 33/72; G01N 33/66
[52] U.S. Cl. ............... 436/67; 210/656; 260/112 B; 422/61
[58] Field of Search ............... 436/67; 422/61; 210/656

[56] References Cited

U.S. PATENT DOCUMENTS 4,243,534  1/1981  Bulbenko ............... 436/67 X
4,269,605  5/1981  Dean ............... 436/67

OTHER PUBLICATIONS

F. Maquart et al., Clinica Chimica Acta, 108(2), 329–332, (1980).

*Primary Examiner*—Sidney Marantz
*Attorney, Agent, or Firm*—Townsend and Townsend

[57] ABSTRACT

An ion exchange method and kit for the separation of hemoglobin $A_{1c}$ from other hemoglobin components in a sample of human blood. The sample is lysed, then used to impregnate a weak cation exchanger. Two buffer solutions are then passed through the column in succession, the first having an alkali metal ion concentration of from about 0.02M to about 0.05M and the second having an alkali metal ion concentration of from about 0.06M to about 0.11M. The second eluate contains substantially all of the hemoglobin $A_{1c}$ and substantially none of the other hemoglobin components in the original sample. Analysis of the second eluate thus provides a reliable indication of the long-term glucose level in the blood of a patient, and hence the patient's ability to regulate the quantity of glucose ingested. The hemolysate with the Schiff base precursor is introduced directly to the chromatographic column.

33 Claims, No Drawings

METHOD AND KIT FOR CHROMATOGRAPHIC SEPARATION OF HEMOGLOBIN A$_{1c}$

BACKGROUND OF THE INVENTION

1. Field of the Invention

This invention relates to the monitoring of long-term blood glucose levels in patients afflicted with diabetes mellitus and to related diagnostic and screening procedures. In particular, this invention relates to a method of isolating hemoglobin A$_{1c}$ from other glycosylated hemoglobin components present in human blood.

It has been known for some time that the quantity of hemoglobin A$_1$ (HbA$_1$), a glycosylated form of adult hemoglobin (HbA), is higher in the blood of diabetic persons than in that of normal persons. Hemoglobin A$_1$ itself consists of several components, of which the main ones have been identified as HbA$_{1a}$, HbA$_{1b}$, and HbA$_{1c}$. These three are known as the "fast hemoglobins," since they elute through a chromatographic column relatively quickly. The fast hemoglobin present in the largest amount is HbA$_{1c}$, which is also known to be the most reliable indicator of the blood glucose level. It is also known that the precursor to HbA$_{1c}$ is a labile adduct in which the linkage between the glucose molecules and the hemoglobin molecule is an aldimine linkage (hereinafter referred to as a "Schiff base"). Due to the high reaction rate involved in its formation from glucose and hemoglobin A as well as its high tendency to dissociate back to these starting materials, the Schiff base level reflects short-term fluctuations in the blood glucose levels, rather than the long-term levels sought to be determined in a meaningful diabetic analysis. For this reason, analyses without Schiff base removal are often poor indications of a patient's ability to regulate glucose.

When analyzing glycosylated hemoglobin, it is, therefore, desirable to separate HbA$_{1c}$ both from its Schiff base precursor and from other glycosylated hemoglobins in order to obtain an accurate and reliable indication of long-term glucose regulation.

2. Description of the Prior Art

A general discussion of glycosylated hemoglobins and their relevance to diabetes mellitus is offered by Bunn, et al., Science, 200, pp. 21–27 (1978). The use of ion exchange resins is described by Chou, et al., Clin. Chem., 24(10), pp. 1708–1710 (1978) and in a series of U.S. patents to Acuff: Nos. 4,142,855, 4,142,856, 4,142,857 and 4,142,858 (all issued on March 6, 1978), 4,168,147 (issued on September 18, 1979) and 4,238,196 (issued on December 9, 1980).

Known methods for removing Schiff base adducts include saline incubation of erythrocytes and dialysis of the hemolysate. The former is described by Goldstein, et al., *Diabetes*, 29, pp. 623–628 (1980), Svendsen, et al., *Diabetologia*, 19, pp. 130–136 (1980) and Chou, et al., *Clin. Chem.*, 24(10), pp. 1708–1710 (1978). The latter is described by Goldstein, et al., supra, and Widness, et al, *J. Lab. Clin. Med.*, 95(3), pp. 386–394 (1980).

Accurate analysis for HbA$_{1c}$ without prior removal of Schiff base has been achieved by a colorimetric technique using acid hydrolysis followed by treatment with thiobarbituric acid. This is described in Svendsen, et al., supra.

SUMMARY OF THE INVENTION

A method is provided for the separation of hemoglobin A$_{1c}$ from its Schiff base precursor and from other glycosylated hemoglobins which avoids the necessity for saline washes, hemolysate dialysis or complicated analytical techniques. The method involves the use of two distinct elution buffers passed successively through a cation exchanger. The resulting separation is quickly and easily performed, providing a more reliable and more accurate determination of long-term glucose levels in human blood free from short-term fluctuations and interfering species.

DESCRIPTION OF THE PREFERRRED EMBODIMENTS

The present invention resides in a method for the separation of hemoglobin A$_{1c}$ from other glycosylated hemoglobins and from its Schiff base precursor in a sample of human blood, comprising the following steps:

(a) The red blood cells in the sample are lysed to form a hemolysate.

(b) A weak cation exchanger is impregnated with the hemolysate.

(c) A first buffer solution is passed through the impregnated cation exchanger in sufficient quantity and of appropriate composition to dissociate unstable complexes to HbA and to preferentially elute interfering substances other than HbA$_{1c}$ out of the exchanger leaving behind HbA$_{1c}$ and HbA. The buffer solution which accomplishes this is one which contains ions of an alkali metal at a concentration of from about 0.02 M to about 0.05 M.

(d) A second buffer solution is then applied which preferentially elutes HbA$_{1c}$. This solution contains dissolved ions of an alkali metal at a concentration of from about 0.05 M to about 0.11 M.

The volumes of the first and second buffer solutions can be adjusted by routine experimentation to result in a second eluate which contains substantially all of the HbA$_{1c}$ originally present in the hemolysate and substantially none of the other hemoglobin components, glycosylated or otherwise. The HbA$_{1c}$ content of the second eluate is then readily determined by conventional means of analysis.

Each step of the method will now be described in detail in the order in which it is performed.

Lysing of the red blood cells can be accomplished by applying a hemolysis technique to the entire blood sample or to any portion thereof which contains all or substantially all of the red blood cells. Centrifugation can be used to separate the red blood cells from the bulk of the sample, although lysing can be readily achieved without such separation with no resulting detriment to the accuracy of the final analysis. Thus, it will be most convenient to apply the hemolysis technique to the entire sample.

Any technique which will rupture the membranes of the red blood cells sufficiently to release the cell contents to the external fluid will suffice. This includes any conventional hemolysis technique. A preferred technique involves the addition of an aqueous detergent solution, followed by incubating the resulting mixture at approximately room temperature for at least about ten minutes.

Once hemolysis has occurred, the hemolysate is used to impregnate a weak cation exchanger. Although any conventional configuration can be used, the cation exchanger is preferably arranged in a vertical column as a fixed bed through which liquids are capable of passing. The volume of hemolysate will most conveniently be several orders of magnitude smaller than the volume of the cation exchanger bed, so that full interaction between the hemolysate and the cation exchanger particles is achieved and ample opportunity exists for ion exchange and component separation during the two elutions. Typically, the sample will permeate only the entry region of the cation exchanger bed, leaving the remainder of the bed for further interaction during the elution process.

A variety of cation exchangers can be used, preferably a weak cation exchanger with a weakly acidic character. Examples of active groups providing a weakly acidic character are carboxylic, methyl carboxylic, and phosphoric acid groups. Examples of resin matrices include acrylic, methacrylic, and phenolic polymers, as well as polystyrene, polyvinyl compounds, cellulose and agarose. A preferred cation exchanger is a copolymer of methacrylic acid and divinylbenzene.

The particle size of the resin is not critical, and will vary with the type of column used. For vertical columns operating by gravitational flow of the buffer solutions, it will be most convenient to use particles of a size between 100 and 400 mesh (U.S. Sieve Series), preferably 200-400 mesh.

When a copolymer of methacrylic acid and divinylbenzene is used as the cation exchanger, it is preferred that about 30% to about 50%, most preferably about 35% to about 45%, of the active sites on the cation exchanger are occupied by ions of an alkali metal, the remainder being occupied by hydrogen ions. The term "alkali metal" is intended to designate the metals of Group 1-A of the periodic table. Preferred metals are those with an atomic weight equal to or less than that of potassium. Of these, sodium and potassium are particularly preferred and sodium is the most preferred. Adjustment of the ionic ratio is conveniently achieved. Such adjustment must be completed prior to impregnation.

Once the ion exchanger is impregnated with the hemolysate, the first of two buffer solutions is passed through the exchanger. Any conventional anionic buffer can be used which is compatible with the alkali metal cation at the concentration of the latter on the active sites of the exchanger without causing an appreciable salting effect, which is capable of maintaining a pH level within the desired range, and which will not degrade the blood sample. The most critical feature of the elution buffer is its alkali metal ion content. As on the exchanger itself, alkali metals with an atomic weight equal to or less than that of potassium are preferred, with sodium and potassium particularly preferred and sodium the most preferred. Although the range of alkali cation concentration appropriate to achieve the desired separation will depend upon the particular alkali cation used, a suitable concentration will generally lie within the range of about 0.02 M to about 0.05 M, preferably about 0.03 M to about 0.04 M.

The pH of the first elution buffer is subject only to the need to avoid hydrolysis of the hemoglobin by excess acidity and to effect the desired separation. With these considerations in mind, the pH of the elution buffer will generally fall within the range of about 5.0 to about 7.5, preferably from about 6.5 to about 7.0. Any conventional buffer system with a pH within this range can be used. Examples include biochemical buffers, zwitterionics, and phosphate buffers. Preferred buffers are potassium and sodium phosphates, both monobasic and dibasic. Sodium phosphates are particularly preferred.

The temperature considerations of the process are similar to those of any ion exchange process. The appropriate operating temperature will thus depend on the volume of exchanger in the column, the particle size and alkali metal content of the exchanger, the surface area and other similar variables and can be readily determined by routine experimentation. It will be most convenient to operate at a temperature within the range of about 14° C. to about 35° C., preferably from about 17° C. to about 30° C., most preferably from about 20° C. to about 28° C.

The volume and flow rate of first elution buffer to be passed through the exchanger bed will be selected to provide the optimum separation. Both the optimum volume and the optimum flow rate of the elution buffer can be readily determined by routine experimentation.

Finally, various conventional stabilizers can be included in the buffer solution, notably sodium azide and/or ethylenediamine tetraacetic acid, in conventional amounts.

Once the first elution has been completed, the eluate is set aside and a second elution buffer is passed through the resin to collect a second eluate which is kept separate from the first. The second elution buffer is similar to the first except for a higher concentration of alkali metal ions. Depending upon the alkali metal used, the metal ion concentration in this second buffer solution will range from about 0.06 M to about 0.11 M, preferably from about 0.07 M to about 0.09 M. Again, any metal ion of Group 1-A of the periodic table can be used, preferably one with a molecular weight equal to or less than that of potassium, with sodium and potassium particularly preferred and sodium the most preferred. It is preferred that the alkali metal ion used on the resin and in each of the two elution buffers be the same.

The pH of the second elution buffer is subject to the same considerations as that of the first. Preferably, however, it lies within the range of about 1 pH unit below the isoelectric point of $HbA_{1c}$ to about the isoelectric point itself. More preferably, the pH ranges from about 0.5 pH unit below the isoelectric point of $HbA_{1c}$ to about the isoelectric point itself. The temperature considerations of the second elution buffer are the same as those of the first, described above.

In a similar manner, the elution volume should be that amount sufficient to separate substantially all of the $HbA_{1c}$ remaining on the resin after the first elution and leave substantially all of the unglycosylated hemoglobin. As before, the elution volume and flow rate appropriate for the particular system used are readily determined by routine experimentation.

An optional improvement in separation efficiency of the unstable glucose complexes from $HbA_{1c}$ can be achieved by including in the liquid solution a chemical species which has an affinity for vicinal diols, and will thus attach to the glucose moiety. Any such species soluble in the buffer solution and inert except for its affinity for the glucose moieties can be used.

Preferred species are dihydroxyboryl compounds, such as boric acid and lower alkyl boronic acids. To enhance the separation, the species is dissolved in any of the liquid solutions involved in the process—the hemolysate, the elution buffers, or a combination of these. With the dihydroxyboryl compound present in the hemolysate, it is preferred to maintain a pH within about 4.5 to about 6.5, more preferably about 5.0 to 6.0, by adding base. The appropriate amount of the dihydroxyboryl compound present will depend upon the extent to which it is needed, i.e., the separation efficiency of the resin itself. When used, the concentration of dihydroxyboryl compound will generally fall within the range of from about 0.01 M to about 1.00 M in the hemolysate or either of the two buffers. When a detergent is used as the hemolysis reagent a quantity of dihydroxyboryl compound ranging from about 0.1 M to about 1.0 M based on the hemolysate is conveniently included in the detergent solution. In the elution buffers, the quantity of dihydroxyboryl compound will generally range from about 0.01 M to about 0.10 M, preferably from about 0.01 M to about 0.03 M.

Once the second elution is complete, the resulting eluate will contain substantially all of the $HbA_{1c}$ present in the original sample and substantially none of the other hemoglobin components. The eluate can then be analyzed for its $HbA_{1c}$ content by any conventional technique, notably biochemical techniques and spectrophotometric techniques, well known in the art.

The following examples are offered to further illustrate the invention and are intended neither to limit nor define the invention in any manner.

EXAMPLE 1

This example demonstrates the efficacy of a dual buffer method according to the present invention in removing Schiff-base-bound glucose from hemoglobin and in separating $HbA_{1c}$ from the other hemoglobin fractions in samples of whole human blood. In this experiment, Schiff base formation was induced by incubating whole blood samples with several different amounts of glucose at 30° C. for six hours. The extent of Schiff base removal was compared against the amount removed by the saline washing technique of the prior art.

A. Schiff Base Removal by Prior Art Technique

A 500 μl aliquot of each of the glucose-treated whole blood samples was washed three times with 10 ml of a physiological saline solution. After each wash, the aliquots were centrifuged and decanted. After the second decantation, 10 ml of physiological saline was added and the mixture was incubated for 4¼ hours at 37° C. After a third decantation, 200 μl of physiological saline was added to the packed cells.

B. Hemolysis

Both the washed samples and the unwashed samples were then lysed by combining a well-mixed 100 μl aliquot of each with 500 μl of a hemolysis reagent consisting of a 0.33% (by volume) aqueous solution of a polyoxyethylene ether surfactant bearing the trade name "Triton X-100" (Rohm and Haas Co., Philadelphia, Pa.), vortexing the mixture and allowing it to stand for at least five minutes. A 20 μl aliquot of each hemolysate was then set aside for comparison with the eluted samples obtained in the following steps.

C. $HbA_{1c}$ Separation

A series of ion exchange resin columns were prepared as follows: Bio-Rex 70 ion exchange resin, a weakly acidic resin consisting of a copolymer of methacrylic acid and divinylbenzene, obtainable from Bio-Rad Laboratories, Richmond, Calif., was conditioned with phosphoric acid to achieve a 55:45 ratio of hydrogen ions to sodium ions at the active sites of the resin. A plastic resin column, approximately 12 cm in length with a volumetric capacity of approximately 12 ml and containing a frit near the bottom, was charged with 1.0 g (3.0 ml) of the preconditioned resin. The column was shaken to provide a uniform suspension. Immediately after shaking, the cap at the top of the column was removed and the tip at the bottom was snapped off to permit the column to drain into a waste container.

Once the column was drained, a 100 μl aliquot of hemolysate was transferred by pipet onto the center of the top of the resin bed. The bed was then allowed to stand for 5–7 minutes.

A first elution buffer solution was then passed through the column. The solution contained 0.023 M phosphate buffer with a pH of 6.7 and a sodium ion concentration of 37 meq/L. A total of 5.0 ml of the solution was used, the first ml of which was added dropwise to the top of the column and the remainder directed in a stream against the column wall. The eluate was discarded.

Once the column had been completely drained of the first elution buffer solution, a second elution buffer solution was passed through the column. The second solution contained 0.05 M phosphate buffer with a pH of 6.7 and a sodium ion concentration of 74 meq/L. This solution was added and allowed to drain through the resin bed in the same manner as the first solution, except that a total of 10.0 ml was used.

Once the column had been completely drained of the second buffer solution, the eluate was mixed thoroughly and transferred to a cuvette with a 10 mm light path and its absorbance read on a laboratory spectrophotometer at 415 nm which had been zeroed with the second elution buffer as a blank.

To express the hemoglobin content in the second eluate as a percentage of the total hemoglobin present in the original sample, a similar absorbance measurement was taken on the hemolysate aliquot which had been set aside (see: last sentence under "Hemolysis" section above) after dilution with the second elution buffer. The percent in the eluate was then determined by the following formula:

$$\text{Percent hemoglobin in eluate} = \frac{\text{Absorbance of eluate}}{5 \times (\text{Absorbance of hemolysate})} \times 100$$

This represents the level of $HbA_{1c}$ as a percentage of the total hemoglobin in the original sample. Both the washed and the unwashed hemolysates were eluted by this procedure.

D. $HbA_{1a,b,c}$ Separation

In order to determine the total Schiff Base present in the original samples, the prior art single buffer elution was used. Due to the ionic strength of this buffer and the hydrogen ion to sodium ion ratio in the exchanger, all of the fast hemoglobins ($HbA_{1a}$, $HbA_{1b}$ and $HbA_{1c}$) collect in the eluate including Schiff base adducts.

The same ion exchange resin with a slightly lower ratio of hydrogen ions to sodium ions was used and the hemolysate was placed on the resin bed in the same manner as before. The elution buffer consisted of 0.05 M phosphate buffer with a pH of 6.7 and a sodium ion concentration of 74 meq/L. A total of 4.0 ml was used.

As before, hemolysates from both the washed and unwashed red blood cells were eluted by this procedure. Analysis of the eluate gave the total of three fast hemoglobins plus Schiff base adducts. Comparison of the eluates from samples unwashed prior to hemolysis against those from samples washed prior to hemolysis provided an indication of the total Schiff base in the original samples.

The results of these analyses are listed in Table 1.1, below, where it is evident that the increase in $HbA_{1c}$ with increasing glucose treatment is much less than the increase in $HbA_1$. This indicates that the two-buffer method of the present invention is a more reliable indicator of the long-term glucose content in blood.

TABLE 1.1

Glycosylated Hemoglobin As Determined By Two-Buffer Method vs. One-Buffer Method

| Quantity of Glucose Added (mg/dl) | $HbA_{1c}$ by Two-Buffer Method | | $HbA_1$ by One-Buffer Method | |
|---|---|---|---|---|
| | Unwashed (%)* | Washed (%)* | Unwashed (%)* | Washed (%)* |
| 0 | 5.20 | 5.07 | 8.24 | 7.58 |
| 250 | 5.38 | 5.06 | 9.25 | 7.48 |
| 500 | 5.34 | 5.20 | 10.33 | 7.69 |
| 750 | 5.56 | 5.09 | 11.38 | 7.77 |
| 1000 | 5.85 | 4.93 | 11.96 | 7.63 |

*Percentage of total hemoglobin in original blood sample.

E. Percent of Total Schiff Base Removed by the Two-Buffer Method

The values determined above were inserted into the following formula to calculate the amount of Schiff base removed by the two-buffer method as a percent of the total amount originally present in the blood sample:

$$\text{Percent Schiff Base Removed} = \frac{\left[\frac{\%\ HbA_1\ \text{unwashed}}{\%\ HbA_1\ \text{washed}}\right] - \left[\frac{\%\ HbA_{1c}\ \text{unwashed}}{\%\ HbA_{1c}\ \text{washed}}\right]}{\left[\frac{\%\ HbA_1\ \text{unwashed}}{\%\ HbA_1\ \text{washed}}\right] - 1} \times 100$$

The results are listed in Table 1.2 below, where it is evident that most of the Schiff base was removed in each case.

TABLE 1.2

Percent Of Total Schiff Base Removed By Two-Buffer Method

| Quantity of Glucose Added (mg/dl) | % Schiff Base Removed |
|---|---|
| 0 | 70.6 |
| 250 | 73.3 |
| 500 | 92.2 |
| 750 | 80.1 |
| 1000 | 67.1 |

EXAMPLE 2

This example demonstrates the effect of the inclusion of borate ion in the hemolysate and in the first elution buffer.

Whole blood samples from four nondiabetic persons were split into two portions apiece. One portion from each pair was incubated with 900 mg/dl of glucose for five hours at 37° C. These portions were then used as samples containing Schiff base. The remaining portions were stored at 4° C. until assay time, whereupon they were used as samples without Schiff base (the actual amount of Schiff base in these samples was negligible, since they were obtained from normal persons and were eighteen days past drawing).

Aliquots of both the incubated and unincubated samples were then lysed and separated in ion exchange columns and dual buffer systems in the same manner described in Example 1, above, under Section C. Four different experiments were run on each sample, using varying amounts of borate ion in both the hemolysis reagent and the first elution buffer as follows:

TABLE 2.1

Borate Ion Content of Reagents

| Experiment | Borate Ion Concentration | |
|---|---|---|
| | Hemolysis Reagent | First Elution Buffer |
| A | 0.6M (pH 5.00) | 0.023M |
| B | 0.6M (pH 5.00) | — |
| C | — | 0.077M |
| D | — | 0.023M |

The reagents were otherwise uniform: the hemolysis reagent was used in a 500 μl quantity and contained 0.33% (by volume) Triton X-100; the first elution buffer was used in a 4.0 ml quantity and contained 0.025 M phosphate buffer at pH 6.7 with a sodium ion concentration of 39 meq/L; and the second elution buffer was used in a 10.0 ml quantity and contained 0.06 M phosphate buffer at pH 6.7 with a sodium ion concentration of 87 meq/L. The resin bed itself was modified slightly in each case from the 55:45 ($H^+$:$Na^+$) ratio used in Example 1, to provide the optimum separation of the $HbA_{1c}$ fraction from the $HbA_{1a}$ and $HbA_{1b}$ fractions. The ratios were selected by analyzing the first and second eluates from columns whose beds had been treated to varying degrees with phosphoric acid. The final ratio in each case lay within the range of 55:45 to 60:40.

The percent $HbA_{1c}$ was determined in each experiment by analysis of the second elution buffer in the manner described in Example 1, above. The results are listed in Table 2.2 for each of the samples tested. Also shown in the table are values for the percent Schiff base removed, derived by the same calculation method used in Example 1, using as an indicator of the total Schiff base present a single buffer elution with 4.0 ml of a 0.05 M phosphate buffer at pH 6.7 and sodium ion concentration of 74 meq/L. It is clear from the table that Schiff base removal is considerably enhanced by using higher concentrations of borate and that the use of borate in the hemolysis reagent is particularly effective.

TABLE 2.2

Borate Ion Inclusion-Test Results Using Two-Buffer Method

| Experiment | Patient | % $HbA_{1c}$ | | % Increase Due to Incubation (Average) | % Schiff Base Removed (Average) |
|---|---|---|---|---|---|
| | | Unincubated Samples | Samples Incubated With 900 mg/ml Glucose | | |
| A | 1 | 5.12 | 5.16 | 0.2 | 99.6 |
| | 2 | 4.75 | 5.01 | | |
| | 3 | 5.84 | 5.53 | | |
| | 4 | 4.44 | 4.46 | | |
| B | 1 | 4.97 | 5.07 | −0.8 | 100 |
| | 2 | 4.83 | 5.04 | | |
| | 3 | 5.86 | 5.53 | | |
| | 4 | 4.49 | 4.32 | | |
| C | 1 | 5.17 | 5.80 | 12.4 | 78.0 |
| | 2 | 5.06 | 5.80 | | |
| | 3 | 5.70 | 6.26 | | |
| | 4 | 4.65 | 5.26 | | |
| D | 1 | 5.17 | 6.04 | 16.5 | 70.8 |
| | 2 | 5.25 | 6.07 | | |
| | 3 | 5.62 | 6.51 | | |

TABLE 2.2-continued

Borate Ion Inclusion-
Test Results Using Two-Buffer Method

| Experiment | Patient | % HbA$_{1c}$ Unincubated Samples | Samples Incubated With 900 mg/ml Glucose | % Increase Due to Incubation (Average) | % Schiff Base Removed (Average) |
|---|---|---|---|---|---|
| | 4 | 4.68 | 5.52 | | |

What is claimed is:

1. A method for the separation of hemoglobin A$_{1c}$ from other glycosylated and nonglycosylated hemoglobins and the Schiff base precursor to hemoglobin A$_{1c}$ in a sample of human blood which comprises:
   (a) lysing the red blood cells contained in said sample to form a hemolysate containing said hemoglobin A$_{1c}$, said glycosylated and nonglycosylated hemoglobins, and said Schiff base precursor,
   (b) impregnating a weak cation exchanger with said hemolysate,
   (c) passing through said exchanger a first buffer solution with ions of an alkali metal dissolved therein at a concentration of from about 0.02 M to about 0.05 M to dissociate said Schiff base precursor into glucose and hemoglobin A and to preferentially elute said glucose and said other glycosylated hemoglobins over said hemoglobin A, said hemoglobin A$_{1c}$ and said other nonglycosylated hemoglobins,
   (d) passing through said exchanger a second buffer solution containing ions of an alkali metal dissolved therein at a concentration of from about 0.06 M to about 0.11 M to preferentially elute said hemoglobin A$_{1c}$ over said hemoglobin A and said other nonglycosylated hemoglobins, and
   (e) recovering the eluate from step (d).

2. A method according to claim 1, in which said cations on said exchanger are alkali metal ions, and said alkali metal ions in said first and second buffer solution are identical in type to each other and to those on said exchanger.

3. A method according to claim 2, in which said alkali metal ions on said exchanger and in said first and second buffer solutions are identical and have an atomic weight equal to or less than that of potassium.

4. A method according to claim 2, in which said alkali metal ions on said exchanger and in said first and second buffer solutions are identical and are selected from the group consisting of sodium and potassium.

5. A method according to claim 2, in which said alkali metal ions on said exchanger and in said first and second buffer solutions are sodium ions.

6. A method according to claim 1, in which said exchanger is a copolymer of methacrylic acid and divinylbenzene and from about 30% to about 50% of the active sites on said exchanger are occupied by ions of an alkali metal.

7. A method according to claim 1, in which the concentration of alkali metal ions in said first buffer solution is from about 0.03 M to about 0.04 M.

8. A method according to claim 1, in which the concentration of alkali metal ions in said second buffer solution is from about 0.07 M to about 0.09 M.

9. A method according to claim 1, in which said exchanger is a copolymer of methacrylic acid and divinylbenzene and from about 30% to about 50% of the active sites on said exchanger are occupied by alkali metal ions, the concentration of alkali metal ions in said first buffer solution is from about 0.03 M to about 0.04 M, the concentration of alkali metal ions in said second buffer solution is from about 0.07 M to about 0.09 M and all of said alkali metal ions are sodium ions.

10. A method according to any of claims 5-9 in which said first and second buffer solutions are phosphate buffers.

11. A method according to any of claims 5-9 in which the pH of said first buffer solution and the pH of said second buffer solution are each within the range of about 6.3 to about 7.3.

12. A method according to claim 1, in which said resin is a polymer of methacrylic acid with a particle size within the range of about 100 to about 400 mesh.

13. A method according to claim 1, in which said resin is a copolymer of methacrylic acid and divinylbenzene with a particle size within the range of about 200 to about 400 mesh.

14. A method according to claim 1, in which steps (c) and (d) are performed at a temperature of from about 14° C. to about 35° C.

15. A method according to claim 1, in which steps (c) and (d) are performed at a temperature of from about 17° C. to about 30° C.

16. A method according to claim 1, in which all of said alkali metal ions are sodium ions, said first and second buffer solutions are phosphate buffers, each with a pH within the range of about 6.3 to about 7.3, said exchanger is a copolymer of methacrylic acid and divinylbenzene on which about 35% to about 45% to whose active sites are occupied by said sodium ions, the concentration of said sodium ions in said first buffer solution is from about 0.03 M to about 0.04 M, the concentration of said sodium ions in said second buffer solution is from about 0.07 M to about 0.09 M and steps (c) and (d) are performed at a temperature of from about 20° C. to about 28° C.

17. A method according to claim 1, in which step (a) is accomplished by adding said sample to an aqueous detergent solution and incubating the resulting mixture at approximately room temperature for at least about ten minutes.

18. A method according to claim 1, in which an effective amount of a dihydroxyboryl compound is present in at least one member selected from the group consisting of said hemolysate prior to step (b), said first buffer solution prior to step (c), and said second buffer solution prior to step (d).

19. A method according to claim 1, in which step (a) is achieved by combining said sample with an aqueous detergent solution, and a dihydroxyboryl compound is added to said detergent solution prior to step (a), to said first buffer solution prior to step (c), or to said second buffer solution prior to step (d), at a concentration of from about 0.01 M to about 1.00 M.

20. A method according to claim 1, in which step (a) is achieved by combining said sample with an aqueous detergent solution, and a dihydroxyboryl compound is added to said detergent solution prior to step (a) at a concentration of from about 0.1 M to about 1.0 M.

21. A method according to claim 1, in which step (a) is achieved by combining said sample with an aqueous detergent solution, and a dihydroxyboryl compound is added to said detergent solution prior to step (a) at a concentration of from about 0.1 M to about 1.0 M, and the pH of said hemolysate is maintained at a value ranging from about 4.5 to about 6.5.

22. A method according to claim 1, in which step (a) is achieved by combining said sample with an aqueous detergent solution, and a dihydroxyboryl compound is added to said detergent solution prior to step (a) at a concentration of from about 0.1 M to about 1.0 M, and the pH of said hemolysate is maintained at about 5.5.

23. A method according to claim 1, in which a dihydroxyboryl compound is added to said first buffer solution prior to step (c) at a concentration of from about 0.01 M to about 0.10 M.

24. A method according to claim 1, in which step (a) is achieved by combining said sample with an aqueous detergent solution, and a dihydroxyboryl compound is added to said detergent solution prior to step (a) at a concentration of from about 0.1 M to about 1.0 M, and to said first buffer solution prior to step (c) at a concentration of from about 0.01 M to about 0.10 M.

25. A method according to claim 1, in which step (a) is achieved by combining said sample with an aqueous detergent solution, and a dihydroxyboryl compound is added to said detergent solution prior to step (a) at a concentration of from about 0.1 M to about 1.0 M, and the pH of said hemolysate is maintained at a value ranging from about 4.5 to about 6.5, and further dihydroxyboryl compound is added to said first buffer solution at a concentration of from about 0.01 M to about 0.10 M.

26. A method according to claim 1, in which step (a) is achieved by combining said sample with an aqueous detergent solution, and a dihydroxyboryl compound is added to said detergent solution prior to step (b) at a concentration of from about 0.1 M to about 1.0 M, and the pH of said hemolysate is maintained at about 5.5, and further dihydroxyboryl compound is added to said first buffer solution at a concentration of from about 0.01 M to about 0.10 M.

27. A method according to any of claims 18-26 in which said dihydroxyboryl compound is selected from the group consisting of boric acid and lower alkyl boronic acids.

28. A method according to any of claims 18-26 in which said dihydroxyboryl compound is boric acid.

29. A method for determining the level of hemoglobin $A_{1c}$ in a sample of human blood containing other glycosylated hemoglobins and the Schiff base precursor to hemoglobin $A_{1c}$ which comprises:
(a) lysing the red blood cells contained in said sample to form a hemolysate containing said hemoglobin $A_{1c}$, said glycosylated and nonglycosylated hemoglobins, and said Schiff base precursor,
(b) impregnating a cation exchanger consisting essentially of a copolymer of methacrylic acid and divinylbenzene about 30% to about 50% of whose active sites are occupied by ions of an alkali metal, the remainder occupied by hydrogen ions, with said hemolysate,
(c) passing through said exchanger a first buffer solution with ions of an alkali metal dissolved therein at a concentration of from about 0.02 M to about 0.05 M to dissociate said Schiff base precursor into glucose and hemoglobin A and to preferentially elute said glucose and said other glycosylated hemoglobins over said hemoglobin A, said hemoglobin $A_{1c}$ and said other nonglycosylated hemoglobins,
(d) passing through said exchanger a second buffer solution containing ions of an alkali metal dissolved therein at a concentration of from about 0.06 M to about 0.11 M to preferentially elute said hemoglobin $A_{1c}$ over said hemoglobin A and said other nonglycosylated hemoglobins, and
(e) analyzing the eluate from step (d) for hemoglobin $A_{1c}$.

30. A method for determining the level of hemoglobin $A_{1c}$ in a sample of human blood containing other glycosylated hemoglobins and the Schiff base precursor to hemoglobin $A_{1c}$ which comprises:
(a) lysing the red blood cells contained in said sample to form a hemolysate containing said hemoglobin $A_{1c}$, said glycosylated and nonglycosylated hemoglobins, and said Schiff base precursor, by adding said sample to an aqueous solution of a detergent consisting essentially of a polyoxyethylene ether surfactant and further containing from about 0.1 M to about 1.0 M boric acid adjusted to pH of about 5.5,
(b) impregnating a cation exchanger with said hemolysate, said cation exchanger consisting essentially of a copolymer of methacrylic acid and divinylbenzene with a particle size within the range of about 100 to about 400 mesh and about 30% to about 50% of whose active sites are occupied by sodium ions, the remainder occupied by hydrogen ions,
(c) passing through said exchanger a first phosphate buffer solution with sodium ions dissolved therein at a concentration of from about 0.03 M to about 0.04 M and further containing from about 0.01 M to about 0.03 M boric acid, the pH of said buffer solution ranging from about 6.5 to about 7.0, to dissociate said Schiff base precursor into glucose and hemoglobin A and to preferentially elute said glucose and said other glycosylated hemoglobins over said hemoglobin A, said hemoglobin $A_{1c}$ and said other nonglycosylated hemoglobins,
(d) passing through said exchanger a second phosphate buffer solution with sodium ions dissolved therein at a concentration of from about 0.07 M to about 0.09 M, the pH of said buffer solution ranging from about 6.5 to about 7.0, to preferentially elute said hemoglobin $A_{1c}$ over said hemoglobin A and said other nonglycosylated hemoglobins, and
(e) analyzing the eluate from step (d) for hemoglobin $A_{1c}$.

31. A kit for use in an assay for determining the hemoglobin $A_{1c}$ content in a sample of human blood without interference from other glycosylated or nonglycosylated hemoglobins or the Schiff base precursor to hemoglobin $A_{1c}$, said kit comprising:
(a) a weak cation exchanger,
(b) a first buffer solution with ions of an alkali metal dissolved therein at a concentration of from about 0.02 M to about 0.05 M, and
(c) a second buffer solution with ions of an alkali metal dissolved therein at a concentration of from about 0.06 M to about 0.11 M.

32. A kit according to claim 31, further comprising a hemolysis reagent comprising an aqueous detergent solution.

33. A kit according to claim 31, further comprising a hemolysis reagent comprising an aqueous detergent solution containing a dihydroxyboryl compound at a concentration of from about 0.1 M to about 1.0 M, and in which said first buffer solution further contains a dihydroxyboryl compound at a concentration of from about 0.01 M to about 0.10 M.

* * * * *